United States Patent
Iwasaki (10) Patent No.: US 10,080,091 B2
(45) Date of Patent: Sep. 18, 2018

(54) SIGNAL PROCESSING DEVICE AND SIGNAL PROCESSING METHOD

(71) Applicant: SONY CORPORATION, Tokyo (JP)

(72) Inventor: Masanori Iwasaki, Kanagawa (JP)

(73) Assignee: SONY CORPORATION, Tokyo (JP)

(*) Notice: Subject to any disclaimer, the term of this patent is extended or adjusted under 35 U.S.C. 154(b) by 0 days.

(21) Appl. No.: 15/329,351

(22) PCT Filed: Aug. 3, 2015

(86) PCT No.: PCT/JP2015/071914
§ 371 (c)(1),
(2) Date: Jan. 26, 2017

(87) PCT Pub. No.: WO2016/024488
PCT Pub. Date: Feb. 18, 2016

(65) Prior Publication Data
US 2017/0215015 A1    Jul. 27, 2017

(30) Foreign Application Priority Data
Aug. 13, 2014  (JP) ................................. 2014-164769

(51) Int. Cl.
*G01B 9/02*    (2006.01)
*H04R 29/00*    (2006.01)
(Continued)

(52) U.S. Cl.
CPC ............... *H04R 29/00* (2013.01); *G01H 9/00* (2013.01); *G10L 25/18* (2013.01)

(58) Field of Classification Search
CPC ............ G01B 9/02007; G01B 9/02087; G01B 9/02094; G01B 9/02095; G01B 9/02096
See application file for complete search history.

(56) References Cited

U.S. PATENT DOCUMENTS 6,417,916 B1 *  7/2002  Dengler ............... G01B 11/161
                                                    324/244.1
8,797,828 B1 *  8/2014  Lev .......................... G01V 8/00
                                                    356/486
(Continued)

FOREIGN PATENT DOCUMENTS

| JP | 2003-121120 A | 4/2003 |
| JP | 2009-014606 A | 1/2009 |
| JP | 2014-074620 A | 4/2014 |

*Primary Examiner* — Jonathan Hansen
(74) *Attorney, Agent, or Firm* — Chip Law Group (57) ABSTRACT

A signal processing device is provided for acquisition of predetermined information. The signal processing device includes a light source unit configured to radiate beams of coherent light having a plurality of wavelengths; an imaging unit configured to capture a speckle image representing an interference state of reflected light caused by the light radiated from the light source unit to an object; and a processing unit configured to process, for each of the wavelengths, the speckle image captured by the imaging unit. The processing unit acquires the predetermined information by analyzing a variation amount of the speckle image acquired for each of the wavelengths. The light source unit radiates beams of light having different wavelengths to a plurality of respective objects. The present technology can be applied to a sensor.

10 Claims, 9 Drawing Sheets

(51) Int. Cl.
  *G01H 9/00* (2006.01)
  *G10L 25/18* (2013.01)

(56) References Cited

U.S. PATENT DOCUMENTS

2010/0226543 A1    9/2010  Zalevsky et al.
2014/0049779 A1*   2/2014  Tin .................. G01B 11/30
                                              356/456

* cited by examiner

|   | 1 | 2 | 3 | 4 |
|---|---|---|---|---|
| 4 | G | Y | G | Y |
| 3 | R | B | R | B |
| 2 | G | Y | G | Y |
| 1 | R | B | R | B |

FIG. 5 (A)

|   | 1 | 2 | 3 | 4 |
|---|---|---|---|---|
| 4 | G | G | Y | Y |
| 3 | G | G | Y | Y |
| 2 | R | R | B | B |
| 1 | R | R | B | B |

SIGNAL PROCESSING DEVICE AND SIGNAL PROCESSING METHOD

CROSS REFERENCE TO RELATED APPLICATIONS

This application is a U.S. National Phase of International Patent Application No. PCT/JP2015/071914 filed on Aug. 3, 2015, which claims priority benefit of Japanese Patent Application No. JP 2014-164769 filed in the Japan Patent Office on Aug. 13, 2014. Each of the above-referenced applications is hereby incorporated herein by reference in its entirety.

TECHNICAL FIELD

The present technology relates to a signal processing device, a signal processing method, and a program. More specifically, the present technology relates to the signal processing device, the signal processing method, and the program that detect vibrations related to sound such as voice.

BACKGROUND ART

In a case where a coarse surface such as a sheet of paper and a wall is irradiated with coherent light such as laser light, and reflected light or transmitted light thereof is observed, a light-dark spot pattern can be found. Such a spot pattern is referred to, for example, as a speckle pattern, simply as a speckle, or as a speckle image. In addition, a phenomenon of producing such a pattern is called, for example, a speckle phenomenon. The study of a property of the speckle phenomenon was started in earnest immediately after the advent of the laser.

Patent Document 1 discloses acquisition of a sound signal from vibrations of a speckle image caused by reflected light of laser light radiated to an object.

CITATION LIST

Patent Document

Patent Document 1: US 2010-0226543

SUMMARY OF THE INVENTION

Problems to be Solved by the Invention

According to the technology disclosed in Patent Document 1, the acquisition can be performed in such a manner that a vibration frequency of the speckle image is converted into a vibration frequency signal of the sound, and signal amplitude is converted into a sound level. However, although a sound from a single object can be measured, it is difficult for the disclosed technology to measure sounds of a plurality of objects.

The present technology has been made in consideration of the above-mentioned circumstances in order to enable measurement of sounds of a plurality of objects.

Solutions to Problems

A signal processing device according to an aspect of the present technology includes: a light source unit configured to radiate beams of coherent light having a plurality of wavelengths; an imaging unit configured to capture a speckle image representing an interference state of reflected light caused by the light radiated from the light source unit; and a processing unit configured to process, for each of the wavelengths, the speckle image captured by the imaging unit.

The processing unit can analyze a variation amount of the speckle image acquired for each of the wavelengths.

The processing unit can separate a signal having each of the wavelengths from a signal having adjacent different wavelengths by means of a difference computation, and can analyze the speckle image of each of the wavelengths using the signal after the separation.

The imaging unit can include a filter that disperses the wavelengths, and the processing unit can process the speckle image subjected to the dispersion using the filter.

The light source unit can include a plurality of light sources that radiates beams of light having different frequencies.

The light source unit can radiate beams of light having different wavelengths to a plurality of respective objects.

The light source unit can radiate beams of light having different wavelengths to a plurality of respective regions.

The processing unit can extract one region of the plurality of regions on the basis of an analysis result, and newly set a plurality of regions within the extracted region, and the light source unit can radiate beams of light having different wavelengths to the plurality of respective newly set regions.

The light source unit can radiate beams of light having different wavelengths to a same site on the object, sites close to each other, a same region, or regions close to each other.

A signal processing method according to an aspect of the present technology includes the steps of: radiating beams of coherent light having a plurality of wavelengths; capturing a speckle image representing an interference state of reflected light caused by the light radiated to an object; and processing the captured speckle image for each of the wavelengths.

A program according to an aspect of the present technology causes a computer to execute a process including the steps of: radiating beams of coherent light having a plurality of wavelengths; capturing a speckle image representing an interference state of reflected light caused by the light radiated to an object; and processing the captured speckle image for each of the wavelengths.

In a signal processing device, a signal processing method, and a program according to an aspect of the present technology: beams of coherent light having a plurality of wavelengths are radiated; a speckle image representing an interference state of reflected light caused by the light radiated to an object is captured; and the captured speckle image is processed for each of the wavelengths.

Effects of the Invention

According to an aspect of the present technology, sounds of a plurality of objects can be measured.

Note that the effects described herein are not necessarily limited, and any of effects described in the present disclosure may be obtained.

BRIEF DESCRIPTION OF DRAWINGS

FIG. 5 (A) and FIG. 5 (B) is a diagram for explaining a color arrangement of a filter.

MODE FOR CARRYING OUT THE INVENTION

Hereinafter, modes for carrying out the present technology (hereinafter referred to as embodiments) will be described. Note that the description will be provided in the following order:

1. CONFIGURATION OF SIGNAL PROCESSING SYSTEM
2. OPERATION OF SIGNAL PROCESSING SYSTEM
3. EMBODIMENT FOR ACQUIRING LIVING BODY INFORMATION
4. REGARDING RECORDING MEDIUM

<Configuration of Signal Processing System>

Figure 1:
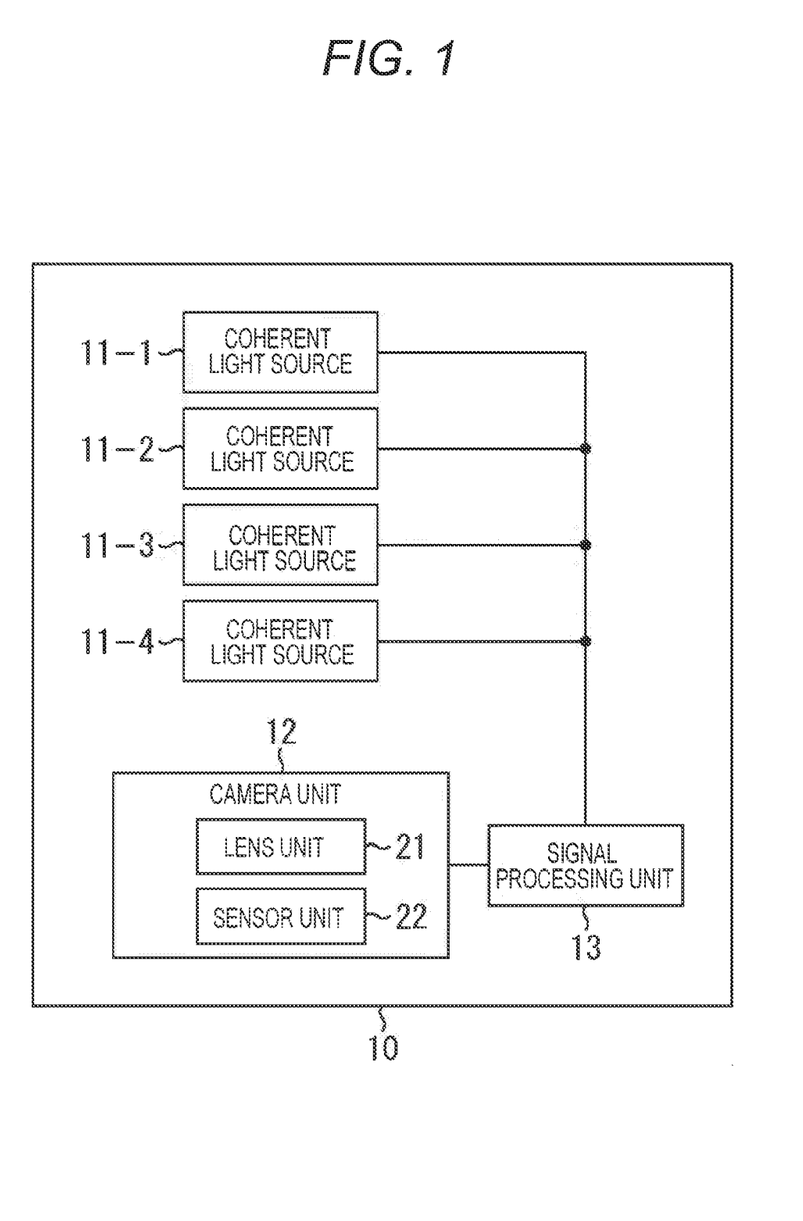
FIG. 1 is a diagram illustrating a configuration of an embodiment of a signal processing device to which the present technology is applied.

FIG. 1 is a diagram illustrating a configuration of an embodiment of a signal processing system to which the present technology is applied. The signal processing system 10 illustrated in FIG. 1 is configured to include coherent light sources 11-1 to 11-4, a camera unit 12, and a signal processing unit 13. In addition, the camera unit 12 is configured to include a lens unit 21 and a sensor unit 22.

The coherent light sources 11-1 to 11-4 are, for example, light sources that emit beams of laser light having predetermined colors. Note that the coherent light sources 11-1 to 11-4 will be simply described as the coherent light source(s) 11 when the coherent light sources 11-1 to 11-4 do not need to be distinguished from one another in the following description.

As described later, the signal processing system 10 to which the present technology is applied irradiates an object with coherent light such as laser light, captures an image (speckle image) caused by the light reflected by the object, and analyzes the image, thereby measuring sound.

The coherent light sources 11 are provided so that the number of coherent light sources 11 corresponds to the number of objects serving as targets for the sound measurement. For example, since the four coherent light sources 11 are provided in the illustration of FIG. 1, they can be used for a process intended for four objects.

The coherent light sources 11-1 to 11-4 are light sources that emit beams of light having different colors. The color is not limited to a visible color (wavelength), and an invisible color can also be used. In addition, light that is likely to cause coherence is used for the coherent light source.

As described above, in a case where N objects serve as the measurement targets, N light sources having N colors of coherence are used as the coherent light sources 11.

The camera unit 12 includes the lens unit 21 and the sensor unit 22, and captures the speckle image to be described later with reference to FIG. 2. The lens unit 21 is configured to include one or more lenses. The sensor unit 22 is configured to include a filter that transmits only the color emitted by the coherent light source 11.

The signal processing unit 13 processes a signal from the camera unit 12. For example, a speckle variation amount is calculated for each of the speckle images of the plurality of light sources, or a characteristic of the object is calculated for each of the light sources.

Note that although the coherent light source 11, the camera unit 12, and the signal processing unit 13 are illustrated to be included in the signal processing system 10 in FIG. 1, the coherent light source 11, the camera unit 12, and the signal processing unit 13 can be configured as the integrally configured device as illustrated in FIG. 1, or may be configured separately.

The coherent light source 11 and the camera unit 12 can be configured separately so that the coherent light source 11 and the camera unit 12 are installed at positions apart from each other. Alternatively, the camera unit 12 and the signal processing unit 13 can also be configured separately so that a signal from the camera unit 12 is supplied to the signal processing unit 13 in a wired or wireless manner.

The speckle image that is captured by the camera unit 12 will be described with reference to FIGS. 2 and 3. A predetermined body in a space represented herein by a coarse body 51 is irradiated with coherent light having a predetermined color from the coherent light source 11. The light with which the coarse body 51 has been irradiated is reflected by the coarse body 51, and the light becomes scattered light. Hereinafter, a wave field formed by the scattered light will be considered.

Figure 2:
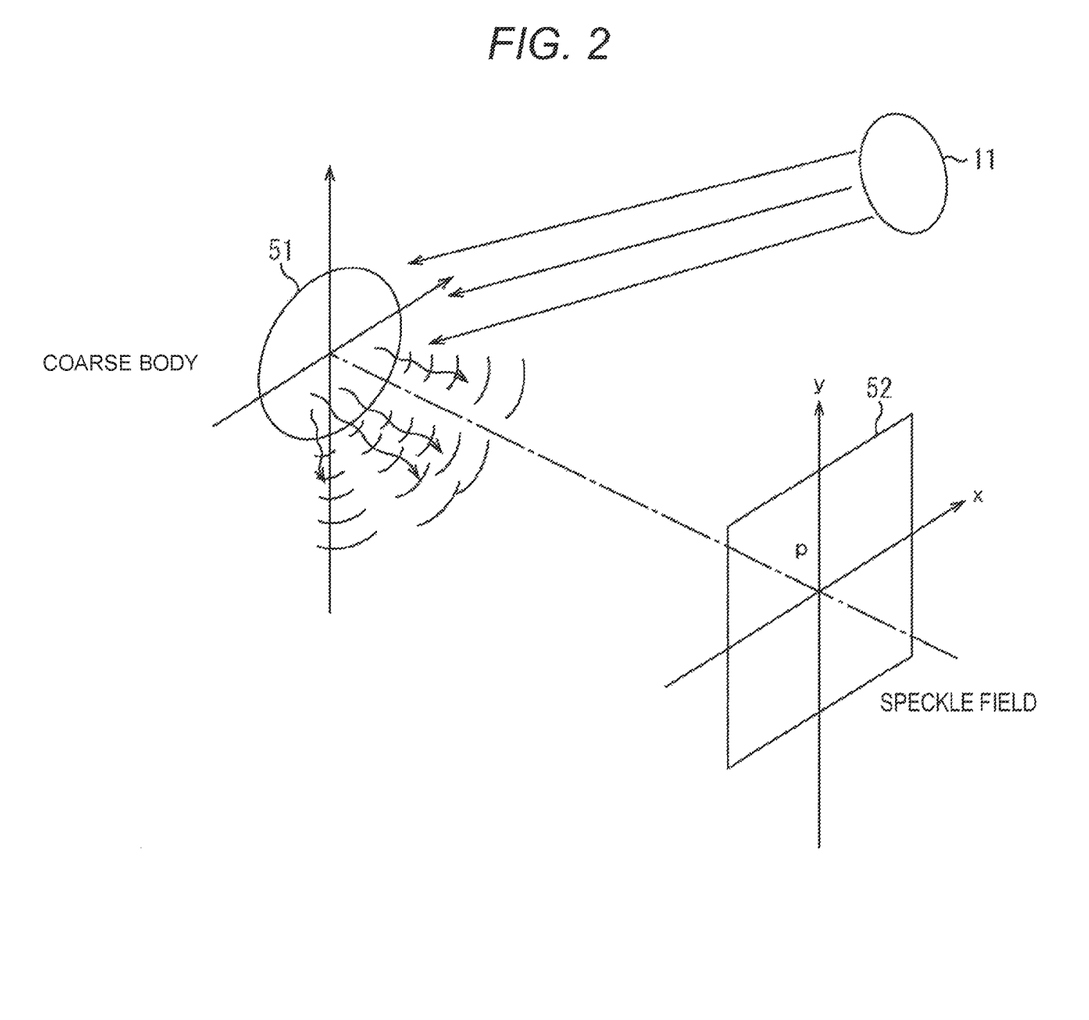
FIG. 2 is a diagram for explaining a principle of measurement by the signal processing device.
Figure 3:
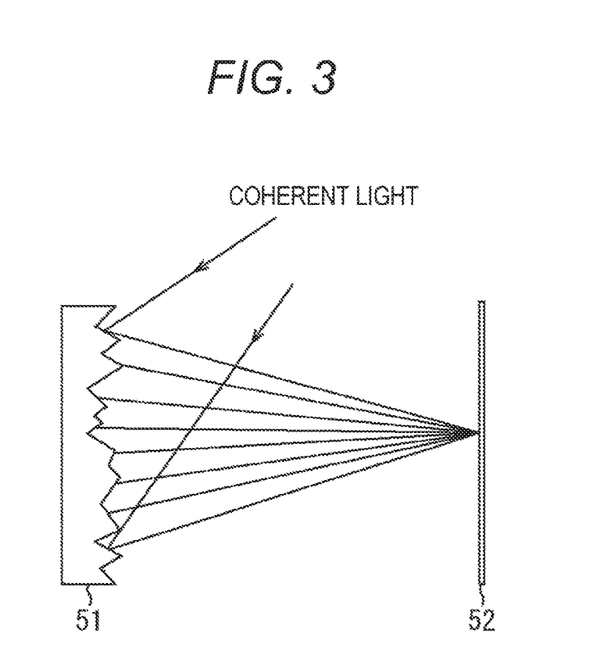
FIG. 3 is a diagram for explaining the principle of the measurement by the signal processing device.

As illustrated in FIG. 3, when the coarse body 51 is irradiated with coherent light such as laser light, a field of light observed at any one point on an observation plane 52, e.g., point P in FIG. 2, is generated in such a manner that a lot of light waves reflected from different places on a coarse surface interfere with one another. Phases of these light waves are random since they reflect irregularity of the rugged coarse surface. Therefore, a spatial intensity distribution of the light caused as the result of the interference is also random.

As a result, a light-dark spot pattern is generated. This spot pattern is referred to, for example, as a speckle (speckle image). The speckle image enters a stationary state (static speckle image) if the body remains stationary, and enters a moving state (dynamic speckle image) if the coarse body 51 moves. The static speckle image or the dynamic speckle image can be observed since it is generated due to the relation with the coarse body 51.

For example, in a case where laser light is used as the coherent light, the laser light has a low entropy since a travelling direction, a phase, and a wavelength of the laser light are fixed. Therefore, the coherent light such as the laser light is used as the light that is used for the observation of the speckle image.

The speckle (unevenness in brightness) does not vary and is fixed if the body illuminated with the coherent light remains stationary. However, if something that even slightly moves and sways is illuminated, the speckle also sways accordingly. This state can be captured by the camera unit 12 (FIG. 1) and observed.

In a case where the speckle image is observed, the camera unit 12 does not capture the coarse body 51 but captures the speckle image on a speckle field (observation plane 52). The speckle field 52 exists when it is apart from the coarse body 51 by a certain distance, and the speckle image on the speckle field 52 can be observed by the camera unit 12. As for the certain distance, a position of the observation plane 52 is apart from the coarse body 51 by a distance longer than the distance represented by the following expression.

$$D^2/4\lambda$$

In this expression, ^2 represents the square, D represents the laser spot size, and λ represents the wavelength. An object plane at which the speckle image is observed, e.g., the observation plane 52, only needs to be provided at a position apart by a distance equal to or longer than the distance represented by this expression.

In this manner, the object is irradiated with the coherent light, and its speckle image is observed, whereby a movement of the object can be observed. For example, assuming that the object is a person, when a throat of the person is irradiated with the coherent light, and its speckle image is observed, a movement of the throat of the person serving as the target can be observed. Since the throat of the person moves while the person is speaking, whether a speaking state occurs or not can be measured when the speckle image related to the throat of the person is observed. Furthermore, the number of vibrations and amplitude or the like are analyzed, whereby speech contents can be analyzed.

The signal processing unit 13 (FIG. 1) of the signal processing system 10 acquires, for example, information such as the above-mentioned number of vibrations and amplitude by analyzing the speckle image captured by the camera unit 12, and further acquires the speech contents by analyzing the information.

Hereinafter, operation or the like of the signal processing system 10 illustrated in FIG. 1 will be described using an exemplary case where the object is a person and the contents spoken by the person are analyzed.

For example, in a case where a throat part of the person is irradiated with coherent light having a predetermined color, e.g., red (R), from the coherent light source 11-1, and a red speckle image is observed by the camera unit 12, the signal processing unit 13 can acquire and analyze a signal of the speckle image caused by the radiated red coherent light by employing a filter that transmits light having a red frequency band in the sensor unit 22 of the camera unit 12.

In a case where light having a single color is used as the coherent light, a single object can be observed. As illustrated in FIG. 1, a plurality of objects is irradiated with respective beams of light having a plurality of colors using the plurality of coherent light sources 11-1 to 11-4, and the speckle images are analyzed on a color basis, whereby the analysis intended for the plurality of objects can be performed.

Figure 4:
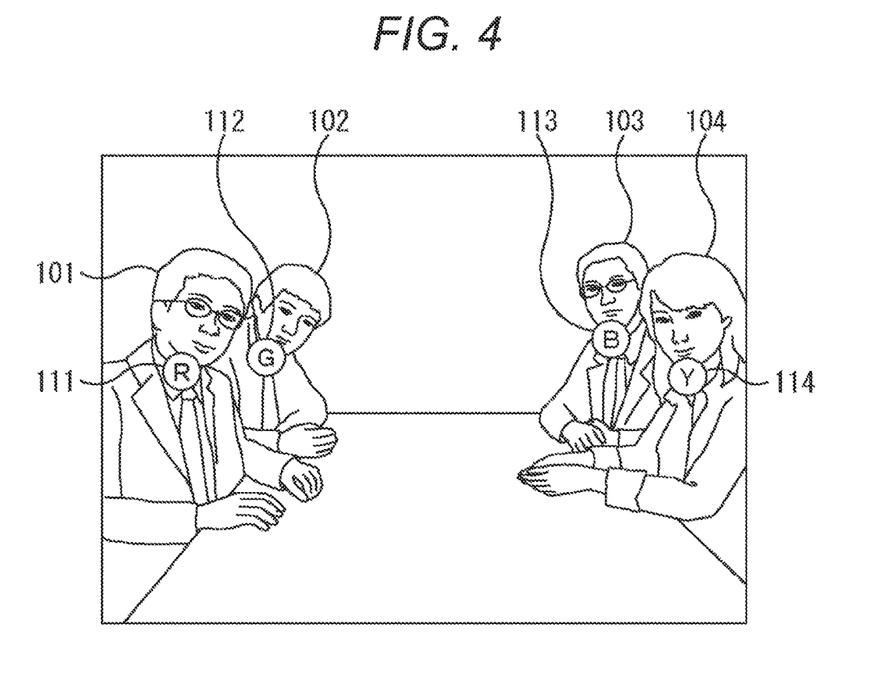
FIG. 4 is a diagram for explaining an object.

For example, a situation illustrated in FIG. 4 will be considered. The situation illustrated in FIG. 4 is a situation in which four persons are present in a predetermined space, and a situation in which speeches by the four persons need to be analyzed by the signal processing system 10 will be considered. The four persons are referred to as a person 101, a person 102, a person 103, and a person 104.

Light radiated from the coherent light source 11-1 reaches a throat part 111 of the person 101. The light is herein assumed to be red (R) light. In the following description, R is appropriately described in the drawings or the like to clearly illustrate the red light. In a similar manner, light radiated from the coherent light source 11-2 reaches a throat part 112 of the person 102. The light is herein assumed to be green (G) light. In the following description, G is appropriately described in the drawings or the like to clearly illustrate the green light.

In a similar manner, light radiated from the coherent light source 11-3 reaches a throat part 113 of the person 103. The light is herein assumed to be blue (B) light. In the following description, B is appropriately described in the drawings or the like to clearly illustrate the blue light. Light radiated from the coherent light source 11-4 reaches a throat part 114 of the person 104. The light is herein assumed to be yellow (Y) light. In the following description, Y is appropriately described in the drawings or the like to clearly illustrate the yellow light.

Figure 5:
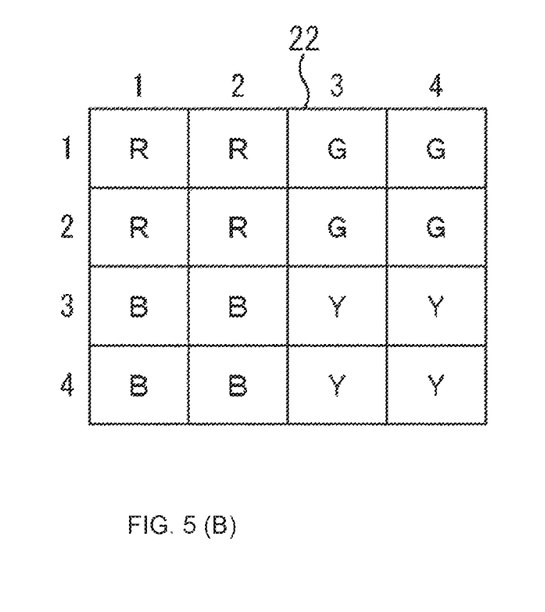

As described above, in a case where the throat parts 111 to 114 of the respective persons 101 to 104 are irradiated with the respective beams of light having the predetermined wavelengths from the coherent light sources 11-1 to 11-4, and movements of the respective throat parts 111 to 114 are detected, the sensor unit 22 of the camera unit 12 has the filter partitioned by the colors as illustrated in FIG. 5 (A) and FIG. 5 (B).

In a case where the beams of red (R), green (G), blue (B) and yellow (Y) light are radiated from the coherent light sources 11-1 to 11-4, respectively, the filter that transmits these colors is provided in the sensor unit 22. The filter is partitioned by the colors into pixels and, for example, arranged as in FIG. 5 (A).

In FIG. 5 (A) and FIG. 5 (B), numbers 1 to 4 provided in each of a lateral direction and a longitudinal direction are numbers provided for denoting row numbers and column numbers, respectively, and numbers provided for the explanation. The row is the lateral direction (horizontal direction) in the drawing, and the row numbers are numbers described on the left side of the drawing in a direction from the upper side to the lower side. The column is the longitudinal direction (vertical direction) in the drawing, and the column numbers are numbers described on the upper side of the drawing in a direction from the left side to the right side. Hereinafter, a pixel at a predetermined position is described as a pixel (row number, column number). For example, a pixel at a first row and a second column is described as a pixel (1, 2), and other pixels are described in a similar manner.

A pixel (1, 1) is a pixel that transmits red light (hereinafter described as an R pixel). A pixel (1, 2) is a pixel that transmits green light (hereinafter described as a G pixel). A pixel (2, 1) is a pixel that transmits blue light (hereinafter described as a B pixel). A pixel (2, 2) is a pixel that transmits yellow light (hereinafter described as a Y pixel).

In this manner, the R pixel, the G pixel, the B pixel, and the Y pixel are assigned to 2×2 pixels, namely, four pixels (hereinafter described as a unit pixel group). A predetermined number of unit pixel groups having the above-mentioned color arrangement are arranged in the longitudinal direction and the lateral direction.

Alternatively, a color arrangement illustrated in FIG. 5 (B) may also be employed. In the color arrangement illustrated in FIG. 5(B), pixels having the same color constitute the 2×2 unit pixel group. The R pixels constitute the unit pixel group including the pixel (1, 1), the pixel (1, 2), the pixel (2, 1), and the pixel (2, 2). The G pixels constitute a unit pixel group including a pixel (1, 3), a pixel (1, 4), a pixel (2, 3), and a pixel (2, 4).

The B pixels constitute a unit pixel group including a pixel (3, 1), a pixel (3, 2), a pixel (4, 1), and a pixel (4, 2). The Y pixels constitute a unit pixel group including a pixel (3, 3), a pixel (3, 4), a pixel (4, 3), and a pixel (4, 4).

In this manner, the filter having such a color arrangement that the unit pixel group includes the same color may be used.

Alternatively, the filter having such a color arrangement that a column or a row includes the same color may be used, although it is not illustrated. For example, the filter having such a color arrangement that the R pixels are arranged in a first row, the G pixels are arranged in a second row, the B pixels are arranged in a third row, and the Y pixels are arranged in a fourth row may be used.

The color arrangements (filters) illustrated herein are only examples, and another color arrangement may be employed as long as the filter can selectively transmit the color of the light used in the coherent light source 11.

Figure 6:
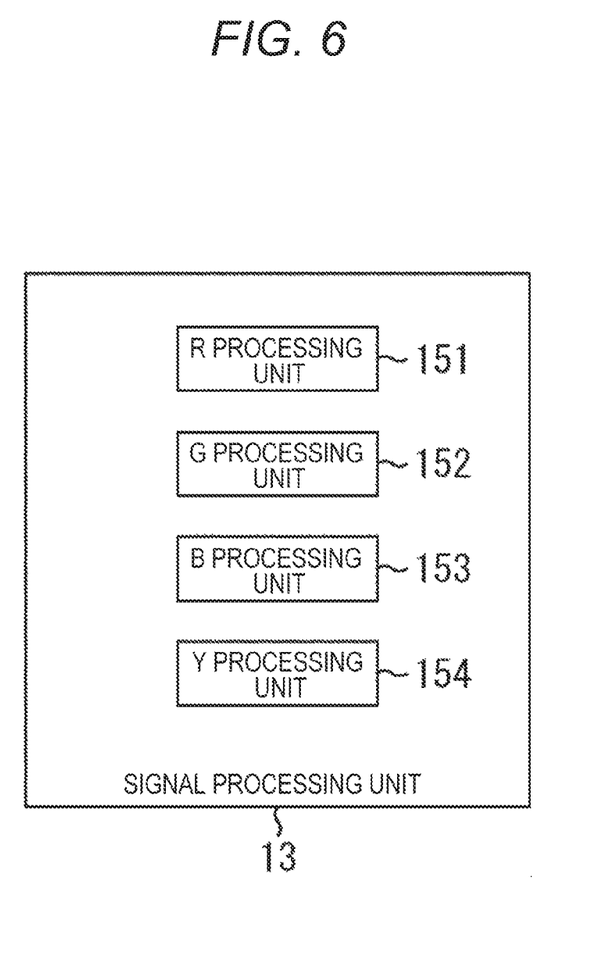
FIG. 6 is a diagram for explaining a configuration of a signal processing unit.

The sensor unit 22 (FIG. 1) of the camera unit 12 includes, for example, the filter having the color arrangement illustrated in FIG. 5 (A), and the signal processing unit 13 has a processing unit that processes signals obtained from the pixels having the same color. In FIG. 6, a configuration of the signal processing unit 13 is illustrated.

The signal processing unit 13 includes an R processing unit 151, a G processing unit 152, a B processing unit 153, and a Y processing unit 154. The R processing unit 151 is a processing unit that processes a signal acquired at the R pixel of the sensor unit 22. The G processing unit 152 is a processing unit that processes a signal acquired at the G pixel of the sensor unit 22. The B processing unit 153 is a processing unit that processes a signal acquired at the B pixel of the sensor unit 22. The Y processing unit 154 is a processing unit that processes a signal acquired at the Y pixel of the sensor unit 22.

In this manner, the signal processing unit 13 has the processing units that process the signals acquired at the sensor unit 22 on a color basis. Note that the signal processing unit 13 may be provided with a separation unit that separates the signals acquired at the sensor unit 22 on a color basis, or the separation unit may be provided in the camera unit 12 so that the signals are supplied to the signal processing unit 13 on a color basis.

Referring again to FIGS. 1, 4, and 6, the person 101 is irradiated with the red (R) coherent light from the coherent light source 11-1. The red coherent light is reflected by the person 101 (throat part 111) to form a red speckle image. The red speckle image is received at the R pixel of the sensor unit 22 of the camera unit 12 and processed by the R processing unit 151 of the signal processing unit 13.

In a similar manner, the person 102 is irradiated with the green (G) coherent light from the coherent light source 11-2. The green coherent light is reflected by the person 102 (throat part 112) to form a green speckle image. The green speckle image is received at the G pixel of the sensor unit 22 of the camera unit 12 and processed by the G processing unit 152 of the signal processing unit 13.

In a similar manner, the person 103 is irradiated with the blue (B) coherent light from the coherent light source 11-3. The blue coherent light is reflected by the person 103 (throat part 113) to form a blue speckle image. The blue speckle image is received at the B pixel of the sensor unit 22 of the camera unit 12 and processed by the B processing unit 153 of the signal processing unit 13.

In a similar manner, the person 104 is irradiated with the yellow (Y) coherent light from the coherent light source 11-4. The yellow coherent light is reflected by the person 104 (throat part 114) to form a yellow speckle image. The yellow speckle image is received at the Y pixel of the sensor unit 22 of the camera unit 12 and processed by the Y processing unit 154 of the signal processing unit 13.

<Operation of Signal Processing System>

Figure 7:
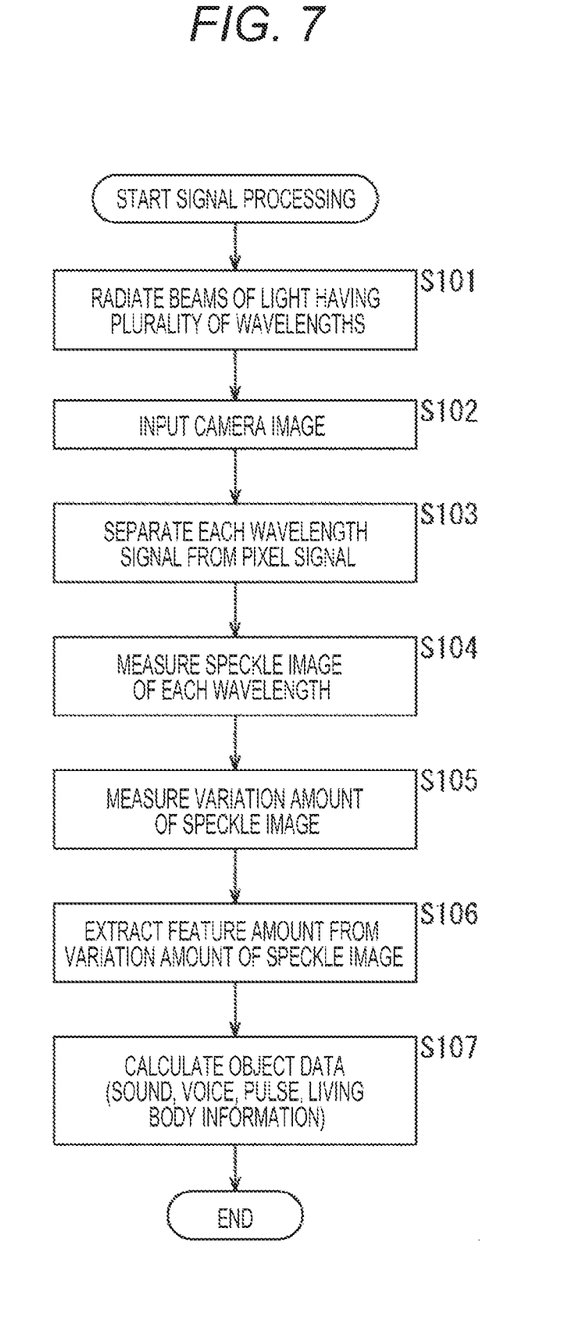
FIG. 7 is a flowchart for explaining operation of the signal processing device.

The operation of the signal processing system 10 illustrated in FIG. 1 will be described with reference to a flowchart illustrated in FIG. 7.

In step S101, the irradiation of the beams of light having the plurality of wavelengths is started. The objects are irradiated with the beams of light having the predetermined colors from the respective light sources, namely, the coherent light sources 11-1 to 11-4. In step S101, the objects are irradiated with the respective beams of coherent light having the different colors. In a case where, for example, three objects exist, the coherent light source 11-1 to the coherent light source 11-3 may be used, and the coherent light source 11-4 may not be used.

In other words, the coherent light sources 11 can be configured to be controlled such that the number of coherent light sources 11 for use is the same as the number of objects.

In step S102, a camera image is input. The speckle image is captured by the camera unit 12. In step S103, each wavelength signal is separated from a pixel signal. As mentioned above, for example, the separation into a pixel signal received at the R pixel, a pixel signal received at the G pixel, a pixel signal received at the B pixel, and a pixel signal received at the Y pixel is performed. The separation may be performed by the camera unit 12 or may be performed by the signal processing unit 13 as mentioned above.

In addition, a difference computation process for an adjacent pixel signal, that is, a process for improving accuracy of each wavelength signal, may be included in the process in step S103. For example, since blue and green are the adjacent colors in the frequency band, a signal component of green light might be included in a signal of blue light received at the B pixel, and a signal component of blue light might be included in a signal of green light received at the G pixel.

Therefore, for example, a process of performing a conversion into a signal including only the signal component of the blue light may be performed as the process of step S103 by subtracting the signal component of the green light from the signal of the blue light received at the B pixel.

Such a process may be performed in a manner similar to that for a process related to complementary color spectroscopy and mixed color correction performed in an imaging device that photographs an object. Spectroscopic performance may be improved by further performing the process related to the complementary color spectroscopy and the mixed color correction or the like, instead of using the light dispersed by the color filter of the sensor unit 22 as it is.

In step S104, the speckle image of each wavelength is measured. The sensor unit 22 is provided with the filter that transmits the color radiated from the coherent light source 11 as described with reference to FIG. 5 (A) and FIG. 5 (B), and the speckle image of each color that has passed through the filter is acquired and processed by the corresponding unit of the signal processing unit 13.

In step S105, a variation amount of the speckle image is measured. Each unit of the signal processing unit 13 measures the variation amount of the input speckle image. Then, in step S106, a feature amount is extracted from the variation amount of the speckle image. The feature amount varies in accordance with what kind of information is acquired eventually. For example, in a case where words spoken by a user need to be analyzed, the feature amount required for the analysis, e.g., the number of vibrations and the vibration amplitude or the like, is extracted.

In step S107, data of the object are calculated. The data of the object are, for example, sound, voice, a pulse, and living body information or the like.

In this manner, the different objects are irradiated with the beams of light having the different wavelengths from the plurality of coherent light sources 11, and the speckle images of the respective beams of light having the different wavelengths are captured and analyzed, whereby items of information are acquired from the respective different objects.

The example illustrated in FIG. 4 has been described using an exemplary case where the four persons 101 to 104 are irradiated with the beams of coherent light having the different four colors, and the contents spoken by the respective persons 101 to 104 are acquired. Next, another example to which the signal processing system 10 (FIG. 1) is applied will be described with reference to FIG. 8.

Figure 8:
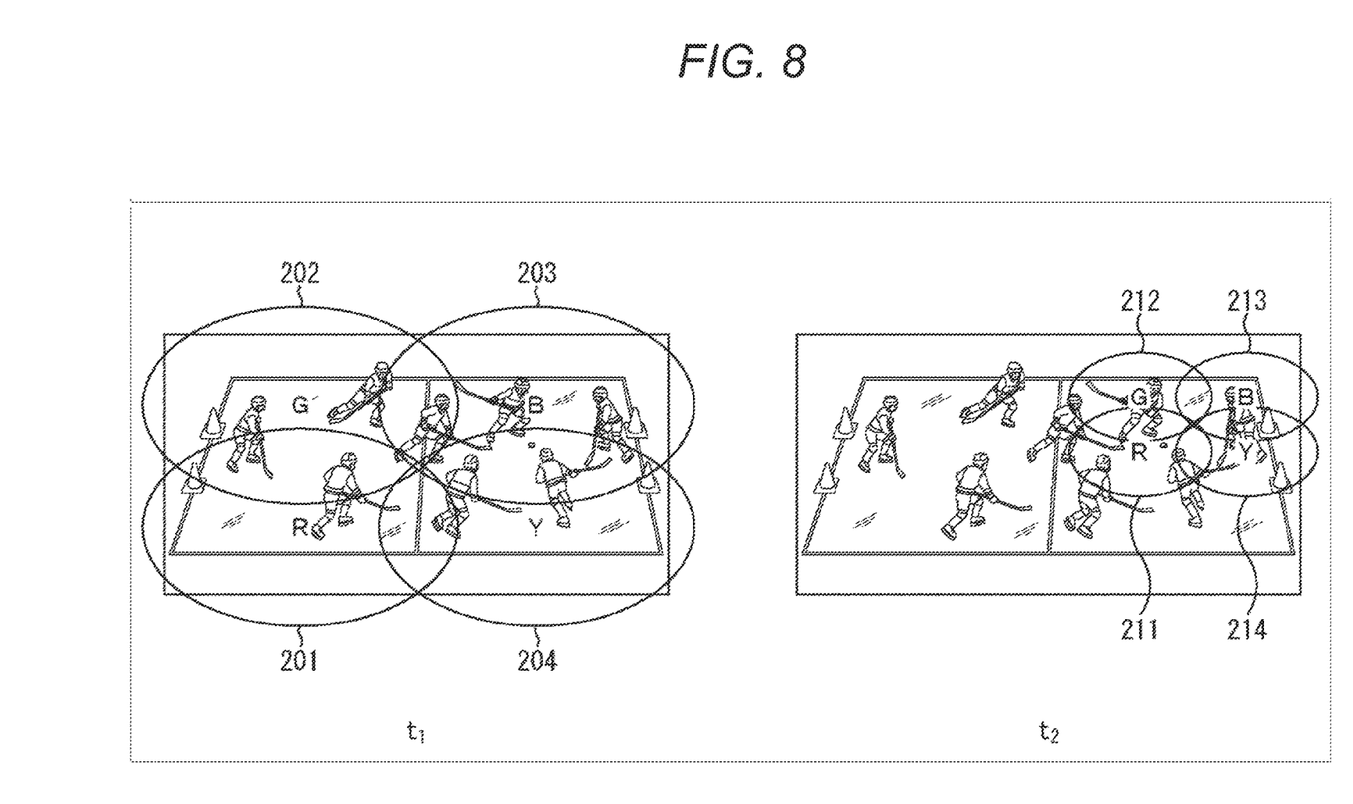
FIG. 8 is a flowchart for explaining narrowing of a region.

In the example illustrated in FIG. 8, a state in which a plurality of persons is dispersed over a relatively wide range is illustrated. In such a state, a case where the range is separated into four regions, and the respective regions are irradiated with the beams of light having the predetermined wavelengths from the coherent light sources 11 will be considered.

In the same way as the above-mentioned case, the description will be continued on the assumption that the red coherent light is radiated from the coherent light source 11-1, the green coherent light is radiated from the coherent light source 11-2, the blue coherent light is radiated from the coherent light source 11-3, and the yellow coherent light is radiated from the coherent light source 11-4.

A region 201 is irradiated with the red (R) coherent light from the coherent light source 11-1. A region 202 is irradiated with the green (G) coherent light from the coherent light source 11-2. A region 203 is irradiated with the blue (B) coherent light from the coherent light source 11-3. A region 204 is irradiated with the yellow (Y) coherent light from the coherent light source 11-4. The regions 201 to 204 may overlap one another.

In this manner, the plurality of regions is irradiated with the beams of coherent light, the speckle images of the respective wavelengths are observed, and the variation amounts thereof are measured. In this case, when a plurality of objects (persons) exists in a single region, for example, a region making a loud sound and a region making a small sound or a region including many persons and a region including only a few persons can be detected through the analysis of the speckle images.

For example, a case where a process of producing an analysis result that regards a region having a large variation amount as a region making a loud sound is performed, and a case where such a region is detected and analyzed in further detail will be considered.

As illustrated in FIG. 8, at time t1, the regions are provided over a relatively wide range, and the respective regions are irradiated with the beams of coherent light. As the result of the analysis of the speckle images obtained through the irradiation, when the analysis shows that the variation amount in the region 203 is larger than those in the other regions 201, 202, and 204, the region 203 is set as a new entire region at time t2, and the process is started.

Specifically, referring to FIG. 8, the region is narrowed at the time t2, and regions 211 to 214 are set in the region where the region 203 has once been positioned. The region 211 is irradiated with the red (R) coherent light from the coherent light source 11-1. The region 212 is irradiated with the green (G) coherent light from the coherent light source 11-2. The region 213 is irradiated with the blue (B) coherent light from the coherent light source 11-3. The region 214 is irradiated with the yellow (Y) coherent light from the coherent light source 11-4.

As described above, in this case, the region making a loud sound is detected while the region is narrowed. If such a process is applied, for example, to a live sport game, a region making a loud sound and estimated to be causing excitement can be extracted. In addition, if such a process is applied to a monitoring camera, a process of detecting a region making a sound and enabling the observation of a person in the detected region can be performed.

In a case of a meeting or the like, a process is executed in such a manner that a region having a large variation amount is detected in an entire meeting room serving as a target at the time t1, the region detected as the region having the large variation amount is set as a new entire region at the time t2, and a region having a large variation amount is detected.

By repeating such a process, a process of detecting persons eventually and producing a state described with reference to FIG. 4 can be executed. In other words, by repeating the narrowing of the region, a process of repeating the narrowing until persons are detected may be executed. In addition, the process of narrowing the region, the process of detecting the persons, and the process of detecting the sounds of the detected persons may be regarded as the different processes, and the processes may be performed while being appropriately switched to one another.

<Embodiment for Acquiring Living Body Information>

Figure 9:
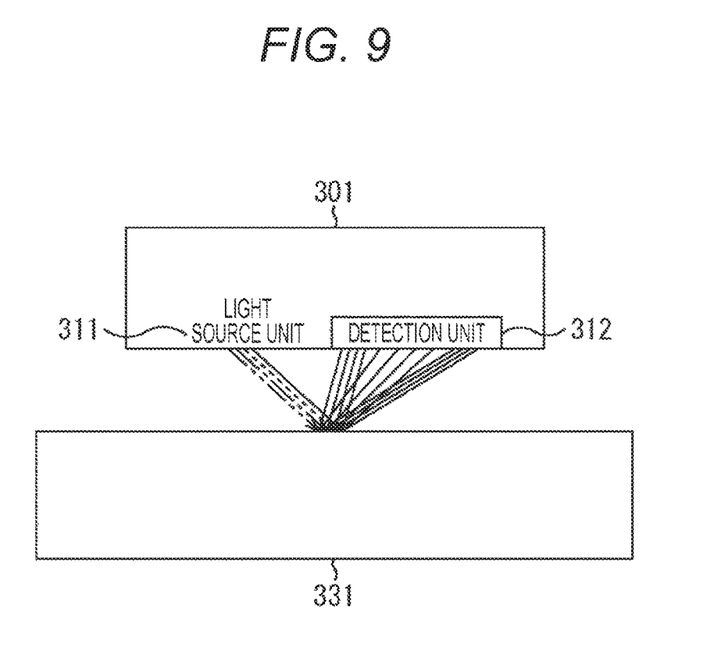
FIG. 9 is a diagram illustrating a configuration of a signal processing device that acquires living body information.

Next, another embodiment of the signal processing system (signal processing device) to which the present technology is applied will be described. By applying the present technology, a signal processing device that acquires living body information of a person can be configured. FIG. 9 is a diagram illustrating a configuration of the signal processing device 301.

The signal processing device 301 includes a light source unit 311 and a detection unit 312. The signal processing device 301 is directed to a predetermined part of a person, e.g., an arm 331, to acquire living body information of the person. The light source unit 311 corresponds to the coherent light source 11 of the signal processing system 10 illustrated in FIG. 1, and irradiates the arm 331 with beams of light having a plurality of wavelengths.

The detection unit 312 corresponds to the camera unit 12 and the signal processing unit 13 of the signal processing system 10 illustrated in FIG. 1, and observes a speckle image generated by the light reflected from the arm 331 to detect predetermined living body information. The living body information to be detected is, for example, a pulse rate, blood pressure, the amount of hemoglobin, and a blood glucose level or the like.

A movement, i.e., flow of blood, is detected, whereby the pulse and the blood pressure can be detected. A speckle image caused by light having a predetermined frequency that has reached blood flow and scattered is analyzed, whereby the hemoglobin and the blood glucose level can be detected.

Figure 10:
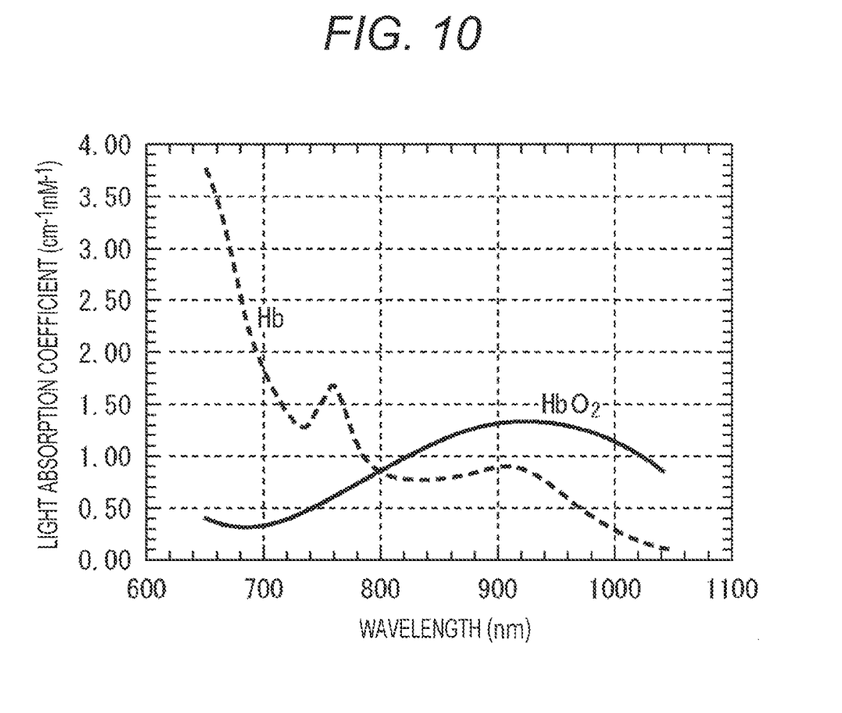
FIG. 10 is a graph of a light absorption spectrum.

For example, a graph representing a relation between a wavelength and a light absorption coefficient with respect to the hemoglobin is illustrated in FIG. 10. In FIG. 10, a horizontal axis represents the wavelength, and a vertical axis represents the light absorption coefficient. In addition, a dotted line in the drawing represents the light absorption coefficient of oxygenated hemoglobin (Hb), and a solid line represents the light absorption coefficient of deoxygenated hemoglobin ($HbO_2$).

For example, a case where light having a wavelength of 700 nm and light having a wavelength of 900 nm are radiated from the light source unit 311 will be considered. It is assumed that the light having the wavelength of 700 nm is radiated, the speckle image generated by the light scattered at the arm 331 is analyzed, and, for example, information about the light absorption coefficient (hereinafter referred to as information A) is acquired. In a similar manner, it is assumed that the light having the wavelength of 900 nm is radiated, the speckle image generated by the light scattered at the arm 331 is analyzed, and, for example, information about the light absorption coefficient (hereinafter referred to as information B) is acquired.

By comparing the information A and the information B, that is, for example, by performing a difference computation, whether blood flowing through the inside of the arm 331 is the oxygenated hemoglobin or the deoxygenated hemoglobin can be detected.

Although the frequency of the light suitable for the information to be detected such as the pulse, the blood pressure, the hemoglobin, and the blood glucose level varies, according to the present technology, the beams of light having the different frequencies are radiated, and the speckle images obtained for the respective frequencies are analyzed, whereby the different items of information can be acquired.

Note that, as mentioned above, in a case where the arm 331 is irradiated with the beams of coherent light, and the plurality of items of information is acquired, the beams of coherent light are preferably radiated to the same place. According to the present technology, when the beams of light having the different wavelengths are radiated from the light source unit 311, the plurality of beams of light can be radiated to the same site (position) or sites (positions) close to each other. Then, the speckle images generated by the respective beams of reflected light of the plurality of beams of light radiated to the same site or the sites close to each other are observed, whereby the plurality of items of information can be acquired.

In other words, according to the present technology, the beams of coherent light having the plurality of wavelengths can be radiated to the same site or the sites close to each other at the same timing, and the plurality of items of information can be obtained at the same site or the sites close to each other at the same timing. Note that the site described herein is not limited to a single point, and may be a region having a predetermined size.

Note that the number of items of information to be detected does not necessarily correspond to the number of beams of coherent light to be radiated when the plurality of items of information is detected. For example, two items of information may be detected in such a manner that two beams of coherent light are used to observe two speckle images, and the respective two observation results are used. Alternatively, a single item of information may be detected in such a manner that an addition or a subtraction is performed using the two observation results. Still alternatively, three items of information may be detected in such a manner that an addition or a subtraction is performed using the two observation results.

Note that although the description has been provided on the assumption that the coherent light sources 11-1 to 11-4 illustrated in FIG. 1 radiate the respective beams of light having the different frequencies, the application range of the present technology is not limited to such a mode that the coherent light sources 11 are provided so that the number of coherent light sources 11 is the same as the number of beams of light to be radiated. For example, the wavelength of the light radiated from the coherent light source 11 may be variable, and the wavelength may be switched at predetermined intervals, so that the beams of light having the plurality of wavelengths are radiated.

In a case where the frequency is switched, and the beams of light having the plurality of frequencies are radiated, the signal processing unit 13 can be configured to observe the variation using the speckle images obtained while the light having a single wavelength is radiated, or can be configured to observe the variation using the speckle images having the same color obtained at predetermined intervals.

The above-mentioned embodiments have been described using an exemplary case where the information such as the sound and the living body information is acquired. However, the present technology can also be applied to a case where other types of information are acquired. In addition, the object is not limited to the person and may be any object.

For example, the present technology can be applied to a plant that serves as the object, so that the amount of water flowing through a leaf vein is measured, or the amount of water on a surface of soil or in the soil is measured. Then, the present technology can be applied to a system that sprinkles water when the amount of water is small.

In addition, the present technology can also be applied to the measurement of the sugar content or the like of a fruit or the like.

In this manner, the present technology can be applied as a sensor that acquires predetermined information.

According to the signal processing device to which the present technology is applied, the plurality of speckle images is observed using the plurality of beams of coherent light. Therefore, using the plurality of persons as the objects, the sounds from the persons can be detected as mentioned above. In addition, for example, using a single person as the target, a plurality of different items of information can be acquired from the person. For example, sound, a heart rate, and a body temperature or the like can be acquired in such a manner that the beams of coherent light having the different wavelengths are radiated, and the speckle images of the respective frequencies are analyzed.

<Regarding Recording Medium>

The above-mentioned sequence of processes can be executed by hardware, and can also be executed by software. In a case where the sequence of processes is executed by the software, a program constituting the software is installed on a computer. As used herein, the computer includes a computer incorporated in dedicated hardware or, for example, a general personal computer or the like that can install various programs to execute various functions.

Figure 11:
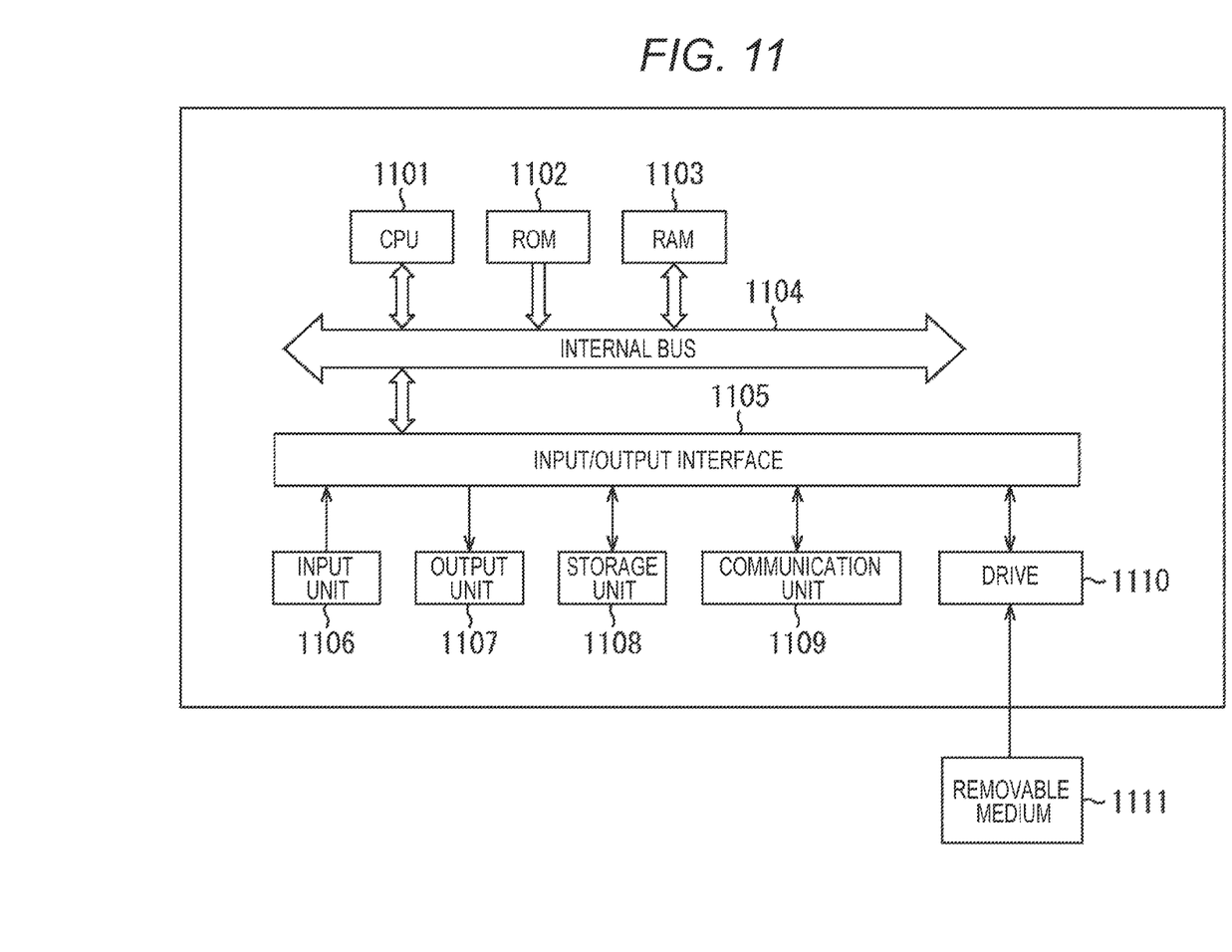
FIG. 11 is a diagram for explaining a recording medium.

FIG. 11 is a block diagram illustrating a configuration example of the hardware of the computer that executes the above-mentioned sequence of processes by means of the program. In the computer, a central processing unit (CPU) 1101, a read only memory (ROM) 1102, and a random access memory (RAM) 1103 are coupled to one another by a bus 1104. An input/output interface 1105 is further connected to the bus 1104. An input unit 1106, an output unit 1107, a storage unit 1108, a communication unit 1109, and a drive 1110 are connected to the input/output interface 1105.

The input unit 1106 includes a keyboard, a mouse, and a microphone or the like. The output unit 1107 includes a display and a speaker or the like. The storage unit 1008 includes a hard disc, a non-volatile memory or the like. The communication unit 1109 includes a network interface or the like. The drive 1110 drives a removable medium 1111 such as a magnetic disc, an optical disc, a magneto-optical disc, or a semiconductor memory.

In the computer configured as mentioned above, the above-mentioned sequence of processes is performed in such a manner that, for example, the CPU 1101 loads the program stored in the storage unit 1108 on the RAM 1103 via the input/output interface 1105 and the bus 1104, and executes the program.

The program that is executed by the computer (CPU 1101) can be recorded in the removable medium 1111 serving as, for example, a package medium or the like, and provided. Alternatively, the program can be provided through a wired or wireless transmission medium such as a local area network, the Internet, and digital satellite broadcasting.

In the computer, the program can be installed on the storage unit 1108 via the input/output interface 1005 when the removable medium 1111 is mounted in the drive 1110. Alternatively, the program can be received at the communication unit 1109 via a wired or wireless transmission medium, and installed on the storage unit 1108. Additionally, the program can be installed in advance on the ROM 1002 or the storage unit 1108.

Note that the program that is executed by the computer may be such a program that the processes are performed in time series in the order described in the present description, or may be such a program that the processes are performed parallelly or at a necessary timing, i.e., for example, when a call is performed.

In addition, the system in the present description represents an entire device including a plurality of devices.

Note that the effects described in the present description are only examples, and are not limited to these effects. Other effects may also be obtained.

Note that the embodiments of the present technology are not limited to the above-mentioned embodiments, and can be variously changed in a range not departing from the gist of the present technology.

Note that the present technology can also be configured as follows.

(1)

A signal processing device including:

a light source unit configured to radiate beams of coherent light having a plurality of wavelengths;

an imaging unit configured to capture a speckle image representing an interference state of reflected light caused by the light radiated from the light source unit to an object; and a processing unit configured to process, for each of the wavelengths, the speckle image captured by the imaging unit.

(2)

The signal processing device according to (1), wherein the processing unit analyzes a variation amount of the speckle image acquired for each of the wavelengths.

(3)

The signal processing device according to (1) or (2), wherein the processing unit separates a signal having each of the wavelengths from a signal having adjacent different wavelengths by means of a difference computation, and analyzes the speckle image of each of the wavelengths using the signal after the separation.

(4)

The signal processing device according to any of (1) to (3), wherein the imaging unit includes a filter that disperses the wavelengths, and the processing unit processes the speckle image subjected to the dispersion using the filter.

(5)

The signal processing device according to any of (1) to (4), wherein the light source unit includes a plurality of light sources that radiates beams of light having different frequencies.

(6)

The signal processing device according to any of (1) to (5), wherein the light source unit radiates beams of light having different wavelengths to a plurality of the respective objects.

(7)

The signal processing device according to any of (1) to (5), wherein the light source unit radiates beams of light having different wavelengths to a plurality of respective regions.

(8)

The signal processing device according to (7), wherein the processing unit extracts one region of the plurality of regions on the basis of an analysis result, and newly sets a plurality of regions within the extracted region, and the light source unit radiates beams of light having different wavelengths to the plurality of respective newly set regions.

(9)

The signal processing device according to (1) to (5), wherein the light source unit radiates beams of light having different wavelengths to a same site on the object, sites close to each other, a same region, or regions close to each other.

(10)

A signal processing method including the steps of:

radiating beams of coherent light having a plurality of wavelengths;

capturing a speckle image representing an interference state of reflected light caused by the light radiated to an object; and processing the captured speckle image for each of the wavelengths.

(11)

A program for causing a computer to execute a process including the steps of:

radiating beams of coherent light having a plurality of wavelengths;

capturing a speckle image representing an interference state of reflected light caused by the light radiated to an object; and processing the captured speckle image for each of the wavelengths.

REFERENCE SIGNS LIST

10 Signal processing system
11 Coherent light
12 Camera unit
13 Signal processing unit
21 Lens unit
22 Sensor unit
151 R processing unit
152 G processing unit
153 B processing unit
154 Y processing unit
301 Signal processing device
311 Light source unit
312 Detection unit

The invention claimed is:

1. A signal processing device, comprising:
a light source unit configured to radiate a plurality of coherent light beams having a plurality of wavelengths;
an imaging unit configured to capture a speckle image corresponding to an interference state of reflected light for each of the plurality of coherent light beams,
wherein the reflected light corresponds to reflection of the plurality of coherent light beams from an object; and
and a processing unit configured to:

separate, based on a difference computation, a first signal of a corresponding captured speckle image from a second signal of the corresponding captured speckle image,
wherein the first signal includes each of the plurality of wavelengths,
wherein the second signal includes at least two wavelengths of the plurality of wavelengths, and
wherein the at least two wavelengths correspond to adjacent colors in a first frequency band;
analyze the corresponding captured speckle image of each of the plurality of wavelengths, based on the separated first signal; and
calculate data corresponding to the object based on the analyzed corresponding captured speckle image.

2. The signal processing device according to claim 1, wherein the processing unit is further configured to analyze a variation amount of the corresponding captured speckle image acquired for each of the plurality of wavelengths.

3. The signal processing device according to claim 1, wherein the imaging unit includes a filter configured to disperse the plurality of wavelengths, and
wherein the processing unit is further configured to analyze the corresponding captured speckle image based on the dispersed plurality of wavelengths.

4. The signal processing device according to claim 1, wherein the light source unit includes a plurality of light sources, and
wherein each of the plurality of light sources is configured to radiate the plurality of coherent light beams having different frequencies.

5. The signal processing device according to claim 1, wherein the light source unit is further configured to radiate the plurality of coherent light beams having different wavelengths to a plurality of objects.

6. The signal processing device according to claim 1, wherein the light source unit is further configured to radiate the plurality of coherent light beams having different wavelengths to a plurality of regions in a capture area of the imaging unit.

7. The signal processing device according to claim 6, wherein the processing unit is further configured to:
 extract at least one region of the plurality of regions based on an analysis result, and
 set a plurality of sub-regions within the extracted at least one region, and
wherein the light source unit is further configured to radiate the plurality of coherent light beams having different wavelengths to the set plurality of sub-regions.

8. The signal processing device according to claim 1, wherein the light source unit is further configured to radiate the plurality of coherent light beams having different wavelengths to one of a site on the object, a plurality of sites on the object that are within a first distance to each other, a region in a capture area of the imaging unit, or a plurality of regions in the capture area of the imaging unit that are within a second distance to each other.

9. A signal processing method, comprising:
in a signal processing device;
radiating a plurality of coherent light beams having a plurality of wavelengths;
capturing a speckle image corresponding to an interference state of reflected light for each of the plurality of coherent light beams,
wherein the reflected light corresponds to reflection of the plurality of coherent light beams from an object;
separating, based on a difference computation, a first signal of a corresponding captured speckle image from a second signal of the corresponding captured speckle image,
wherein the first signal includes each of the plurality of wavelengths,
wherein the second signal includes at least two wavelengths of the plurality of wavelengths, and
wherein the at least two wavelengths correspond to adjacent colors in a first frequency band;
analyzing the corresponding captured speckle image of each of the plurality of wavelengths, based on the separated first signal; and
calculating data corresponding to the object based on the analyzed corresponding captured speckle image.

10. A non-transitory computer-readable medium having stored thereon computer-executable instructions that, when executed by a processor, cause a computer to execute operations, the operations comprising:
controlling a light source unit to radiate a plurality of coherent light beams of coherent light having a plurality of wavelengths;
capturing a speckle image corresponding to an interference state of reflected light for each of the plurality of coherent light beams,
wherein the reflected light corresponds to reflection of the plurality of coherent light beams from an object;
separating, based on a difference computation, a first signal of a corresponding captured speckle image from a second signal of the corresponding captured speckle image,
wherein the first signal includes each of the plurality of wavelengths,
wherein the second signal includes at least two wavelengths of the plurality of wavelengths, and
wherein the at least two wavelengths correspond to adjacent colors in a first frequency band;
analyzing the corresponding captured speckle image of each of the plurality of wavelengths, based on the separated first signal; and
calculating data corresponding to the object based on the analyzed corresponding captured speckle image.

\* \* \* \* \*